United States Patent [19]

Klebe et al.

[11] Patent Number: 5,565,353
[45] Date of Patent: Oct. 15, 1996

[54] PERFUSABLE CULTURE DEVICE

[75] Inventors: Robert J. Klebe, Helotes; Anne M. Grant, San Antonio, both of Tex.

[73] Assignee: Board of Regents, The University of Texas System, Austin, Tex.

[21] Appl. No.: 264,034

[22] Filed: Jun. 22, 1994

[51] Int. Cl.$^6$ .................................................. C12N 5/02
[52] U.S. Cl. .......................... 435/240.25; 435/240.45; 435/298.1; 435/289.1; 435/304.3
[58] Field of Search .......................... 435/288.1, 288.3, 435/288.7, 298.1, 304.1, 304.3, 305.1, 240.25, 240.45, 289.1

[56] References Cited

U.S. PATENT DOCUMENTS

| | | | |
|---|---|---|---|
| 2,940,360 | 6/1960 | Carter | 435/298.1 |
| 2,942,520 | 6/1960 | Rose | 435/288.3 |
| 3,726,597 | 4/1973 | Dvorak et al. | 435/288.3 |
| 3,993,560 | 11/1976 | Halpern | 210/94 |
| 4,334,028 | 6/1982 | Carver | 435/284 |
| 4,530,907 | 7/1985 | Peterson et al. | 435/305.1 |
| 4,734,372 | 3/1988 | Rotman | 435/288.7 |
| 4,770,854 | 9/1988 | Lyman | 422/102 |
| 4,910,151 | 3/1990 | Platt | 436/163 |
| 4,927,764 | 5/1990 | Lyman et al. | 435/296 |
| 5,112,646 | 5/1992 | Koshi et al. | 422/52 |
| 5,139,952 | 8/1982 | Honda et al. | 435/284 |
| 5,240,854 | 8/1993 | Berry et al. | 435/284 |

OTHER PUBLICATIONS

Rose, George, "A Separable and Multipurpose Tissue Culture Chamber," *Tissue Culture Laboratory*, 1075–1083, 1954.

Sykes et al., "A New Chamber for Tissue Culture," *P.S.E.B.M.*, 125–217, 1958.

*Primary Examiner*—David A. Redding
*Attorney, Agent, or Firm*—Arnold, White & Durkee

[57] ABSTRACT

The present application relates generally to methods and devices allowing for high density tissue culture techniques to be practiced. Specifically, the application relates to a perfusable culture device which allows for the maintenance of high-density tissue cultures. The application also details methods of using the device to grow cells of varying densities, and methods of observing cell growth at high densities with time-lapse micrography.

19 Claims, 3 Drawing Sheets

PERFUSABLE CULTURE DEVICE

The U.S. Government has rights in this invention pursuant to NIH Grant No. DE08144.

BACKGROUND OF THE INVENTION

A. Field of the Invention

The present invention relates generally to the field of cell culture. In particular, the invention relates to devices and methods that allow for the growth maintenance of cell cultures at high cell density. Some aspects of the invention involve a perfusable culture device designed so that a constant culture media level is maintained. Other aspects of the invention involve the use of the devices of the invention for time-lapse cinemicrography.

B. Background of the Related Arts

Traditional tissue culture procedures involve growing or maintaining cells in liquid or on solid media in culture flasks. One of the limitations of this type of system has been the fact that it is difficult to grow high-density tissue cultures in such a system.

Cells maintained in culture systems frequently have defined and stringent nutrition needs. In order to meet these needs, it has been necessary to maintain a relatively high media-to-cell ratio. Otherwise, the cells rapidly deplete the media of nutritive components and fill the media with metabolic waste. Further, $CO_2$ gas bubbles build up and obscure the growing cells when one attempts to grow the cells to high density. This leads to difficulty in recording the growth of cells in culture via time lapse photography.

In order to forestall these problems, traditional cell culture has involved growing cells until they are just confluent, then trypsinizing the cells to remove them from the culture vessel and placing a portion of the cells in a new vessel with fresh media. Allowing cells to grow into a higher density is difficult with flasks because once the media becomes low in nutritive value, the cells either die or grow in aberrant manners. There is a current need in the field of cell growth research, e.g. in clinical organogenesis, for a system which allows for the growth of dense tissue cells which are multiple cell-layers thick. One favorable characteristic of such a system could be that it would maintain a constant level of culture media within the device. Unfortunately, there has been no system which readily permits such a constant culture media level.

Another form of culture used by researchers is organ culture, where whole or sliced animal organs are grown in culture media. Organ culture confronts the same problems as cell culture in that the need for nutrients requires a high media-to-cell ratio. Further, organ culture also confronts problems because it is difficult to diffuse nutrients into the center of thicker masses of organ tissue.

One of the current frontiers in the field of cell growth is the study of how cells live and grow in vivo. In vivo, cells are in contact with each other, many of the cells are quiescent, and cells undergo morphogenesis into various tissue types. Each of these states of cell growth and development has been difficult to observe in traditional tissue culture systems. The known culturing systems have not allowed cells to be grown until they reach a quiescent state where morphogenesis can occur. This is because of the constant need to cycle cell media and reduce the number of cells. Further, it has been difficult to study and perform organogenesis, a subset of morphogenesis. In organogenesis, a population of cells morphologically differentiates such that an organ is formed. While there has been some limited success at growing very thin, often single cell thick, layers of skin for medical use. The growth of thicker tissues and organs for clinical use has proven difficult. A large part of this difficulty has been the inability to constantly supply nutrients to the growing cells in a system where the media-to-cell ratio is low.

Time lapse cinemicrography devices provide a valuable tool for the study of cell growth and differentiation. While systems for such studies have been known, the data obtained have been limited since only low density cell cultures have been grown for long periods of time. The prior art tissue culture chambers are not suited for growing high density tissue cultures for periods long enough to allow for tissue morphogenesis to occur.

Prior time lapse cinemicrography studies have usually involved observation of individual cells at high magnification. In such studies, cells have been maintained at very low density since many microscopic features of cells are obscured under confluent conditions. For such studies, the Rose (Rose 1954) and Sykes-Moore chambers (Sykes, et al., 1959) have proven to be quite satisfactory. The present inventors attempted to use the Sykes-Moore chamber for time-lapse studies of cells maintained at very high cell density and found that several problems occurred even when the Sykes-Moore chamber was perfused several times a day with medium delivery by a peristaltic pump. The chief problems encountered were the production of $CO_2$ gas bubbles which interrupted the optical path and resulted in constant defocusing of the system due to the deformation of the coverslip walls of the chamber.

Time-lapse cinemicrography studies of cells maintained at very high cell density in Sykes-Moore chambers even with a medium perfusion system, gave unsatisfactory results for several reasons. First, $CO_2$ produced by cells led to the formation of gas bubbles which often obstructed the optical path. Second, the specimen regularly went out of focus due to gas pressure build up which caused the glass coverslips to warp, and, in some cases, break. Third, after several days cells underwent degenerative changes apparently due to lack of oxygen.

To observe morphological changes in cells maintained at high cell density studies were initiated with Sykes-Moore chambers. In such studies, MDCK cells were planted in Sykes-Moore chambers that had been completely filled with medium and connected to a peristaltic pump which perfused the culture. Gas bubbles formed once cells had become confluent and that the microscope appeared to continually go out of focus in spite of several attempts to bolster the stage lock mechanism.

By sealing all orifices with silicone rubber glue, it was determined that the formation of gas bubbles was not due to a leak in the peristaltic pump tubing or chamber itself. The present inventors concluded that the gas bubbles were due to $CO_2$ produced by the cells. The constant problem of the microscope going out of focus was determined to be due to $CO_2$ pressure deforming the glass coverslips that make up the top and bottom of the Sykes-Moore chamber. Indeed, on several occasions, the glass coverslips of the Sykes-Moore chamber split due to gas pressure build-up.

These problems caused the Sykes-Moore chamber to be of use for only about one day when observing cells at moderately high density. This is too short to allow for dense cultures to grow and for meaningful time-lapse micrography.

The failure of existing technology forced the present inventors to develop a new culture apparatus that would allow cells to grow to high cell density and allow long-term time-lapse cinemicrography.

Initially, Applicants attempted to maintain a constant media level in profusion chambers by having a single culture media inlet and a single culture media outlet, both positioned below the desired fluid level. The idea was that if culture media could be pumped into the device at exactly the same rate it was being pumped out of the device, a constant fluid level would be maintained. While theoretically workable, this configuration proved to be very difficult to place in practice. It was found to be almost impossible to obtain exactly equal inflow and outflow of the media. Therefore, over a period of time, the culture chamber would either fill with media or be drained below the desired level. This can cause at least two problems: (1) cells die in an empty chamber, and (2) even if the chamber were not to become completely empty or full, a constantly shifting media level will obscure the focus necessary for time lapse micrography.

Confronted with these problems, the present inventors created a simple, dependable, and inexpensive system for maintaining high density tissue cultures for a long period of time.

SUMMARY OF THE INVENTION

A simple culture chamber is described which permits cells to be maintained at very high cell density for a week or more. This simple culture vessel allows for long term observation of cells at extremely high cell density and permits an unobscured view of cells for over a week.

In general, the invention relates to a perfusable culture device capable of maintaining a substantially constant culture media level. This device allows for either continuous or intermittent cycling of the media through the culture device. Therefore, fresh media containing nutrients is available to cells growing in the culture device, while aged media collected waste is gradually removed from the culture device. During use, the culture device is typically connected to a pump, which allows the use of a culture media inlet system for injection of new media and a culture media outlet system for the withdrawal of old media on a continuous or intermittent basis. With some applications, it may be desirable to continually pump media into and out of the system. With other applications, it might be desirable to change the medium in the system every few hours or days. Regardless of the timing of the media circulation, the present culture device allows for circulation of the medium in the chamber without disrupting the cells or opening the chamber while maintaining a constant media level.

Generally, the perfusable culture device has a chamber, at least one culture media inlet which flows into the chamber, and at least one culture media outlet which flows out of the chamber.

The chamber can be of almost any liquid-containing material, and can be of almost any shape. For example, the chamber can be made of plastic, glass, metal, or the like. Usually, it will be advantageous to make the chamber out of a transparent material, so that the growing cells can be observed. Further, it is anticipated that plastic or other inexpensive material will be most often employed in the manufacture of the chamber. These materials lend themselves to easy manufacture and are relatively inexpensive such that the culture devices can be disposable. Of course, should certain desirable property qualities be desired, for example, improved optical qualities which could only be obtained with optical quality glass, the chambers may be made of material with these qualities. The chambers may be cylindrical, round, square, rectangular or irregularly shaped. Typically, they will be somewhat flattened so that there is a large service area between the gas space above the media and the media. A large surface area at the bottom of the chamber aids in providing a large space for the growing cells to rest upon. The chamber should be sealable so that microorganisms do not contaminate the culture. The chamber may be fitted with a gas inlet and/or outlet that serves to flow gas to and/or from the chamber and maintain the proper atmosphere. A small gas pressure relief fitting may be included to permit venting of $CO_2$ produced by the cells and to allow air into the system.

In a preferred embodiment of the invention, the chamber will be shaped much as a typical cell culture flask is shaped, e.g., a flattened bottle which is designed to lie on its side and has a neck with a cap on it at one end. Such flasks are well known in the art. Perfusable culture devices according to the invention shaped like culture flasks have the advantage of fitting in and on existing laboratory culture equipment.

There are many different innovations and designs of tissue culture flasks which may be employed as the basis for the present culture device. For example, Lyman, et al., U.S. Pat. No. 4,927,764 details a flask which has improved optical qualities and a top wall which has a large opening covered by a flexible transparent film which can be peeled off to provide access to the flask interior. Carver, U.S. Pat. No. 4,334,028, discusses a flask with a frangible zone formed into the top wall, which allows for easy access to the contents of the flask. Lyman et al., U.S. Pat. No. 4,770,854, describes a laboratory flask with a ramp that allows accessibility to the four corners of the rear wall and the four corners of the growing surface for a scraper. Honda et al., U.S. Pat. No. 5,139,952, describes a flask shaped such that a scraper can reach the entire bottom of the surface area through the neck. These U.S. patents are incorporated by reference herein, for their teachings related to culture flasks. Each of the flasks described above has features which should be of benefit when used in conjunction with Applicants' perfusable culture device. Since the culture device is essentially a culture vessel modified so that culture media can be circulated through it, the advantages of the prior art flasks, when incorporated into the invention, are clear.

The culture media outlet is typically a tube that passes through the wall of the chamber into the interior of the chamber. The outlet allows media to be pumped out of the chamber. The outlet has an exterior portion which is adapted to receive a hose or tube which runs to a pump. The outlet has an interior portion that has a port at the desired media level. The culture media outlet may be formed of metal, glass, plastic, etc. In preferred embodiments of the invention, the culture media inlet enters the chamber in the gas space above the desired liquid level and extends downward to the desired liquid level. This positioning of the culture media outlet prevents liquid leakage at the juncture of the outlet and the chamber wall, and does not interfere with the positioning of the flask on a supporting surface. More than one culture media outlet may be employed in the device, and not all culture media outlets in a device must have a chamber interior port which is positioned at the desired culture media level. Rather, so long as one port is positioned at the culture media level, other ports may be positioned below the desired media level.

The perfusable culture device must have at least one culture media inlet leading from the exterior of the chamber to the interior of the chamber. This inlet is designed so that media can be pumped into the chamber. The inlet may be constructed of any of the materials from which the outlet can be constructed, and is, like the outlet, typically a tubular passage. The culture media inlet has a chamber interior port through which media passes into the chamber. Typically this port is positioned below the desired fluid level, so that the flow of media into the chamber does not disrupt the surface of the fluid. However, in certain applications it may be desirable to position the port above the desired fluid level so that the incoming media drops down into the supply of media in the chamber. The culture media inlet is typically hooked up to a pump which pumps media into the chamber on either a continuous or intermittent basis. The inlet typically enters the chamber in the gas space above the desired liquid level and descends into the media. In this manner, leaks from the junction of the inlet and the chamber are minimized. Of course, more than one culture media inlet may be present in a single device.

One of the inventive aspects of the present invention is its ability to maintain a constant culture media level. A constant level is maintained due to the difference between the media inlet and media outlet capacities of the device. The device is designed so that at least one culture media outlet port is positioned at the desired culture media level and quickly removes any media which would raise the media level above the desired level. This requires that the media outlet capacity is greater than the media inlet capacity. The culture media outlet capacity is determined by summing the total rate of media removal from all of the outlets of a single device. The culture media inlet capacity is the sum of all of the rates of media input from all inlets.

In order for the device to maintain a constant level, the culture media outlet with the media level port positioned at the desired level syphons away any excess media before the fluid level can be raised.

The culture media outlet with the media level port draws fluid only when there is sufficient fluid in the chamber to contact the port. During use, the culture media inlets function to add media to the chamber until the level of the culture media outlet's port at the desired fluid level is reached. At that point, because the culture media outlet capacity is greater than the culture media inlet capacity, any additional fluid that flows into the chamber from the inlets, it is immediately removed and constant fluid level is maintained.

Additional culture media outlets can be used to syphon media from below the desired culture media level, so long as the capacity of any sublevel culture media outlets is less than the capacity of all of the culture media inlets. If the sublevel outlets had a greater capacity than the media inlets, then the fluid level would be reduced to the level of the sublevel outlets. An outlet that has a port at the bottom of the chamber can remove small debris which form during the prolonged cultivation of cells. The fluid level outlet, being positioned at the air-liquid interface, will not remove such small debris. The presence of the bottom level port removes debris which would settle down to the cell layer, and this is of particular use during time-lapse studies where debris could obscure the image of the cells.

In some preferred embodiments of the claim device, there are two culture media inlets. The advantage of this system is that, should one inlet become clogged, the other inlet will permit the continued flow of media into the chamber, albeit at a slower rate.

In certain preferred embodiments, the perfusable device will have two culture media outlets and two culture media inlets, such that the advantages of both of these configurations systems are realized.

The perfusable culture device is typically hooked up to a pump, such that media is pumped into the chamber through each culture media inlet and media is pumped out of the chamber through each culture media outlet. As previously stated, the outlet pump capacity must be greater than the inlet pump capacity in order for the culture device to function properly and maintain a constant media level. Further, the outlet capacity of any below media surface outlets must be less than the total inlet capacity.

A variety of pumps may be used in conjunction with the perfusable culture device. However, it is anticipated that peristaltic pumps will be one of the most convenient forms of pumps to use. Peristaltic pumps are available from many companies, including Masterflex® and Ismatec®. One advantage of peristaltic pumps is that the flow rate from a single culture media outlet or culture media inlet can be controlled by the diameter of tubing attached to that outlet or inlet. Therefore, in order to get an outlet capacity which is greater than the inlet capacity, it is merely necessary to use a larger bore tube attached to the culture media outlet than is attached to the culture media inlet. In one embodiment of the invention, the inventors attach tubes of equal bore to two culture media inlets and a submedia outlet. A larger bore tube is attached to the culture media outlet whose port is at the desired media level. When the tubes are hooked to individual heads on a multihead peristaltic pump, this result is that the culture media outlet capacity is greater than the culture media inlet capacity and the system maintains a constant fluid level. Of course, the invention is in no way limited solely to the use of peristaltic pumps or this manner of controlling the rate of flow, and those of skill in the art will appreciate that there are numerous equivalent arrangements.

Other embodiments of the present invention involve methods of culturing cells at high density. These methods involve obtaining a culture device and adding culture media and cells to be cultured, attaching the culture media outlet(s) and culture media inlet(s) to a pump, and perfusing the chamber by either constantly or intermittently pumping culture media into the chamber through the inlets and pumping culture media out of the chamber through the outlets, thereby maintaining the desired media level in the chamber while replenishing the nutrients in the media and removing waste on a regular basis. The culture device is then placed in a situation facilitating or allowing for cell growth and the cells are allowed to grow.

Other embodiments of the present invention involve methods for performing time-lapse cinemicrography of cell cultures. Using the device of the present claims, it is possible to maintain focus of cells growing at high density for long periods of time. This device avoids $CO_2$ gas bubbles from obscuring the focus and also avoids lack of nutrients and waste accumulation from causing cell growth problems. This cinemicrography is performed by growing cells according to the methods defined above, with the culture device being placed upon the stage of a microscope. Typically, an inverted phase microscope is used. The optical quality of culture devices made of standard culture flask materials is sufficient to allow for observation at 10 to 400 times magnification. 100 times magnification is typically employed by the inventors in their studies. It is possible to obtain higher magnification microscopy, however, with magnifications of 1000 times or more, one might wish to employ a flask or culture device which has improved optical qualities. Such a flask is detailed by Lyman, et al. in U.S. Pat. No. 4,927,764 which is incorporated by reference herein. A camera may be set up to record the course of cell growth through the microscope. Either a film camera or a videotape camera may be employed in this manner. By using a motion picture camera and a timer or a time lapse VCR, it is possible to obtain time-lapse photography of the cells.

BRIEF DESCRIPTION OF THE DRAWINGS

Certain aspects of the invention will become more clear upon the viewing of the accompanied drawings.

DETAILED DESCRIPTION OF THE PREFERRED EMBODIMENT

The following examples detail specific embodiments of the claimed invention. Those with skill in the art will understand that many non-inventive variations of these devices and methods are possible. These variations are within the scope of Applicants' invention and the claims are in no way limited to those embodiments detailed in this section of the application.

The device eliminates problems inherent in existing time-lapse cinemicrography chambers that prevent the use of existing devices for cell cultured at high cell density. Production of $CO_2$ gas by cells grown to high density is sufficient to warp a glass coverslip, resulting in the specimen going out of focus. Warping can become so extreme that the glass coverslips of past systems crack. The device has the addition advantage of allowing one to grow tissue cultures to high density while maintaining a constant volume of medium in the device during frequent automatic medium changes.

EXAMPLE I

Flask-Shaped Culture Profusion Device

Figure 1:
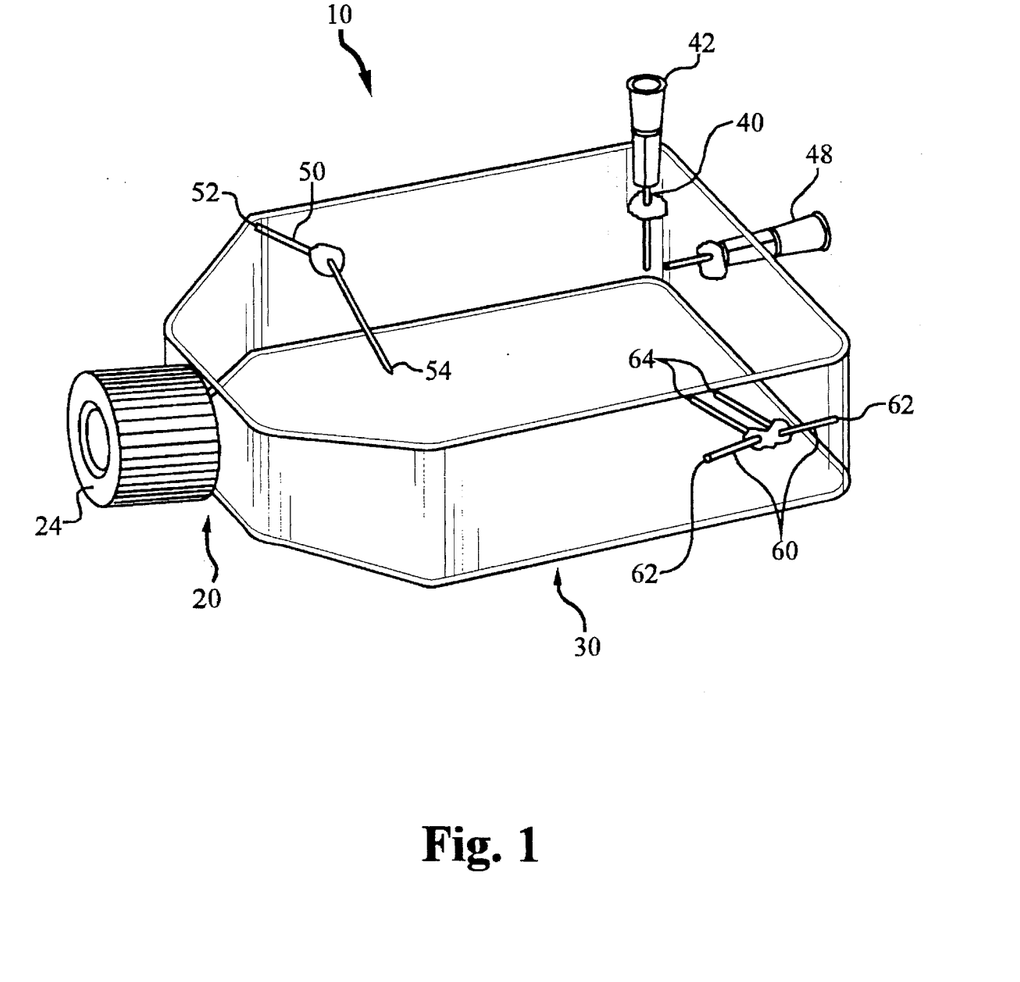
FIG. 1 A perspective view of an embodiment of the perfusable culture device.
Figure 2:
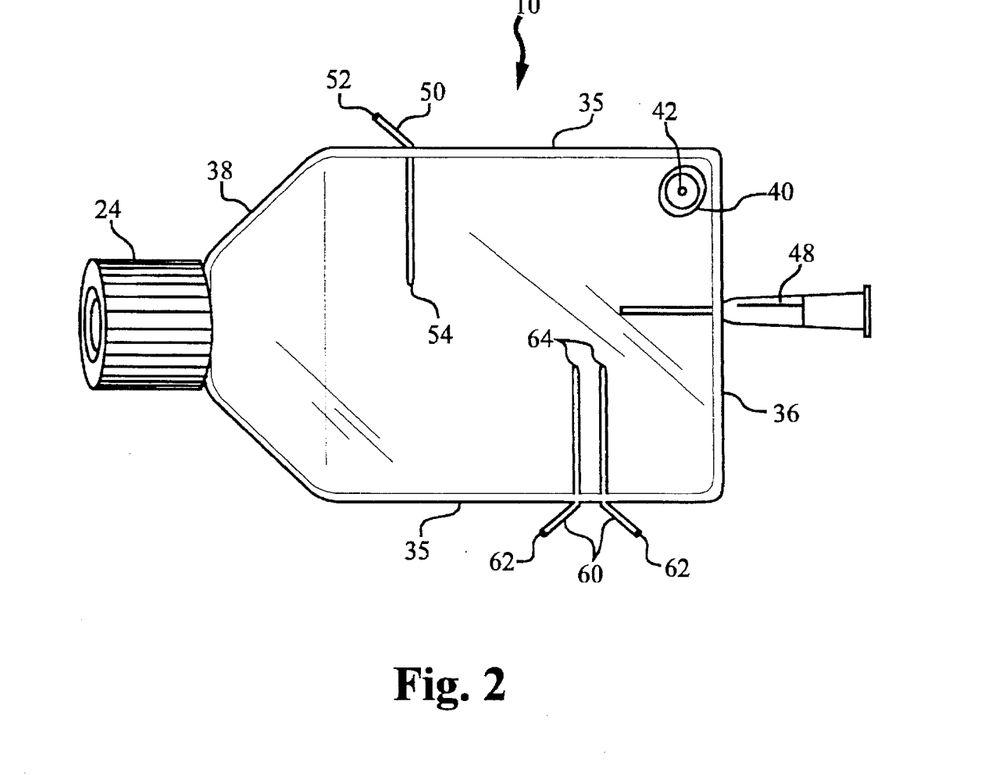
FIG. 2 A top view of embodiment of the perfusable culture device.
Figure 3:
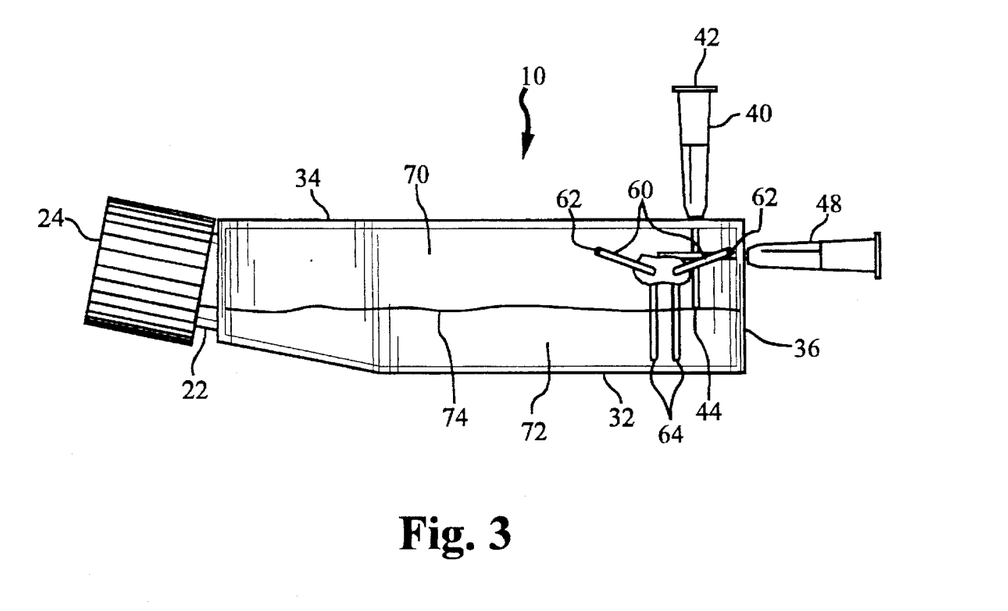
FIG. 3 A side view of embodiment of the perfusable culture device.

One embodiment of the present invention is a flask-shaped, perfusable cultural device. Such a device is illustrated in FIGS. 1, 2 and 3. As can be seen, the device has the general form of a culture flask. The device is typically made of clear plastic material, although it may be made of glass, metal or another non-permeable material. For use in cinemicrography, transparent materials are preferred. Plastic flasks are typically manufactured by injection molding, a technique which is well-suited to the manufacture of the device of the embodiment since it is possible to injection-mold the flask, along with its inlets and outlets. The specifics of the flask-shaped perfusable culture device are as follows.

Perfusable culture device 10, has chamber portion 30, outlets 40 and 50, inlets 60, and neck region 20.

Chamber portion 30 has bottom 32, top 34, side walls 35, rear wall 36, and neck proximal walls 38. Neck 22 projects at an upward angle from neck walls 38. The chamber typically has a 25 cm$^2$ surface area.

Neck region 20 comprises neck 22 and cap 24. Neck 22 is designed such that cap 24 screws or snaps securely onto neck Cap 24 may form a gas-tight seal between itself and neck 22, because tissue culture often requires a specific gas environment above the tissue media. For example, a 5 to 10% $CO_2$ concentration is often required for cell culture. In order to help maintain the desired gas environment by allowing excess $CO_2$ to escape, vent 48

Top outlet 40 is a tubular outlet having external port 42 and internal port 44. In the Figures, top outlet 40 is formed of a hypodermic needle with the Leur-lock fitting still in place. In FIGS. 1 and 2, top outlet 40 enters chamber 30 through top 34. Top outlet 40 is positioned such that internal port 44 is at the desired media liquid level. While top outlet 40 can enter chamber 30 from any angle through any wall or side, it is preferable that top outlet 40 enter the chamber in gas space 70, so that any media leaks between the juncture of top outlet 40 and chamber 30 are minimized. Top outlet 40, as with other outlets and inlets in the invention, can be made of varying materials. The inventors have used metal outlets which have been cemented or glued in place in some prototypes of the invention. These outlets have worked well, however, it is somewhat difficult to obtain a solid seal between the metal outlets and the plastic chamber wall. The inventors have helped remedy this problem by bending outlets and inlets at the portion that passes through the wall of the chamber. When these bent outlets and inlets are glued in place, they are difficult to pull out, and a solid seal is achieved. Applicants anticipate that outlets can be injection molded at the same time as the chamber, thereby forming a continuous piece of plastic-type material forming both outlets 40 and 50, inlets 60, and chamber 30.

Outlet 50 has external port 52 and internal port 54. Internal port 54 is positioned such that it is below the desired liquid level 74. Outlet 50 can enter chamber 30 through any wall or side. In the illustration, outlet 50 enters the chamber through side wall 35. Although the illustration shows outlet 50 entering the chamber below the desired fluid level 74, if outlet 50 enters the chamber in gas space 70 and then extends below liquid level 74, the risk of leakage between the junction of outlet 50 and chamber 30 is reduced. Outlet 50 is not a required part of all embodiments of the invention. Outlet 50, when employed, may serve to remove debris from the bottom of the flask.

Inlets 60 allow for culture media to be fed into chamber 30. This embodiment of the device has two inlets 60, thereby having a back-up should one inlet become clogged. Inlet 60 has external port 62, and internal port 64. Inlet 60 can enter chamber 30 through any wall or side, however, in the illustrated embodiments inlets 60 enter the chamber through side wall 35. As with outlets 40 and 50, certain advantages are realized if inlets 60 enter chamber 30 in gas space 70 and then pass into the media reservoir.

Figure 4:
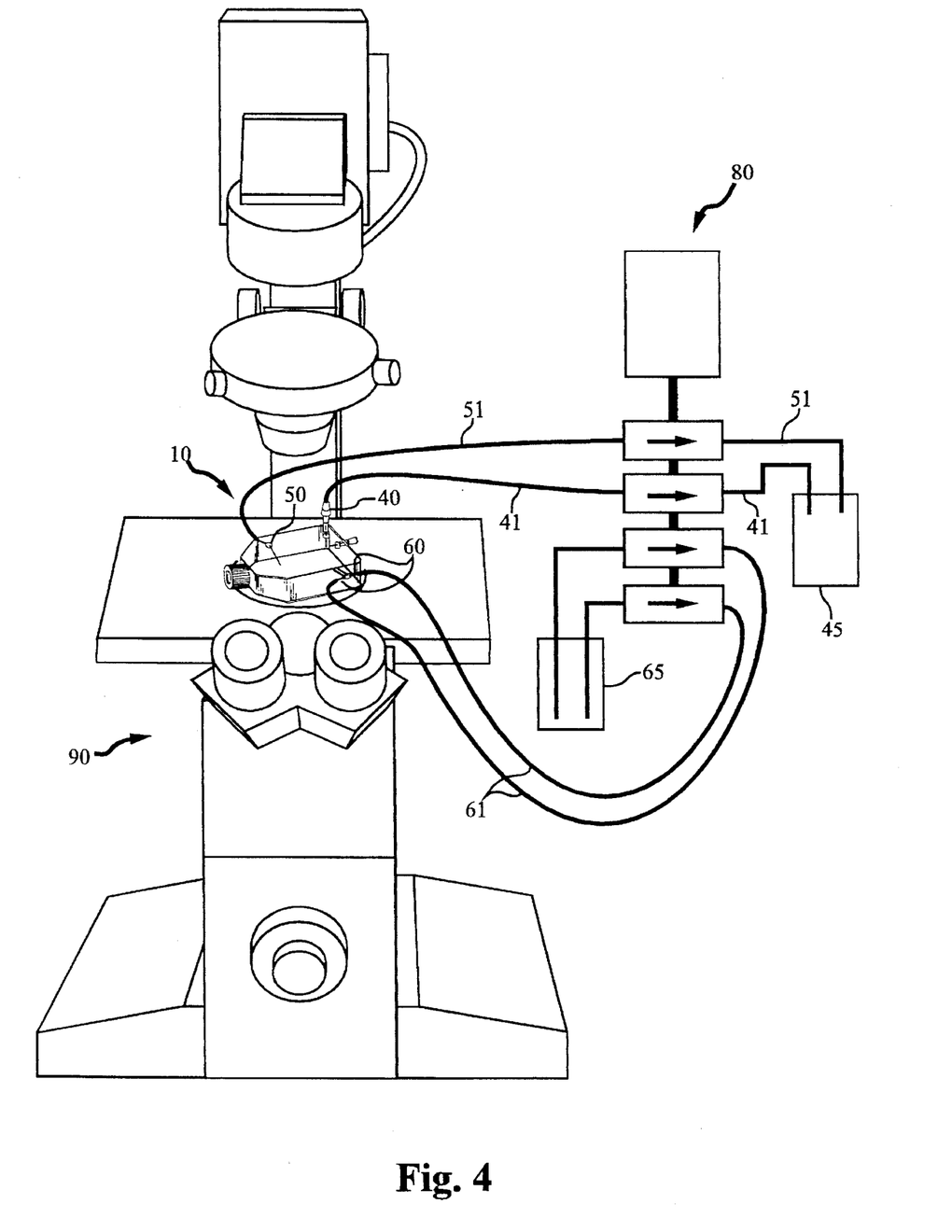
FIG. 4 A view of one embodiment of the culture device hooked up to a peristaltic pump in an operating configuration.

The combined capacity of outlets 40 and 50 must be greater than the combined capacity of inlets 60 in order for a constant media level to be maintained. Further, in order for the constant media level to be maintained at the level of internal port 44, the capacity of outlet 50 must be less than the combined capacity of inlets 60. The inventors have obtained these differences in capacity by hooking a peristaltic pump with the outlets and inlets of the same diameter to tubing of appropriate diameters. During use, outlets 40 and 50 are hooked up to a pump such that media can be moved from the flask through them. As shown in FIG. 4, fluid level outlet 40 is hooked up to fluid level outlet tube 41, and outlet 50 is hooked up to outlet tube 51. Inlets 60 are hooked up to a pump and media reservoir via inlet tubes 61, such that media can be introduced into the chamber through them. When the pump(s) is operating, outlet 40 functions to maintain a constant media level. As additional media is added through inlets 60, outlet 40 syphons away any media rising to the level of outlet port 44. Since the total outlet capacity is greater than the total inlet capacity, but the capacity of outlet is less than the capacity of inlets 60, the media level will constantly be maintained at the level of port 44.

During use, for the device may be placed in the configuration shown in FIG. 4. The device 10 is placed upon the stage of a microscope 90. Inlet tubes 61 are attached to the media inlets 60. Outlet tube 41 is attached to fluid level outlet 40, while outlet tube 51 is attached to outlet 50. Inlet tubes 61 are connected to pump 80, in such a way that they can draw fresh media from media reservoir 65. Outlet tubes 41 and 51 are connected to pump 80 and then to waste media container 45. A camera can be positioned so as to allow for still pictures or cinemicrography.

EXAMPLE II

Manufacture and Use of a Prototype Culture Chamber

Materials

A. Equipment-although brands of equipment and some model numbers are given, Applicants in no way limit their claims to these specific pieces of equipment.
Peristaltic pump, Model G-07521-50, Cole Parmer
Four Easy-Load pump heads, Model G-07518-00, Cole Parmer
Timer, 6 events/day, 1 minute resolution,
Inverted phase microscope,
Television camera,
Time lapse tape recorder, Panasonic
$CO_2$-incubator, National Appliance
37° C. warm room (or similar devise for maintaining cultures at 37° during time lapse observations).

B. Supplies
PharMed® peristaltic pump tubing, size 13, Cole Parmer
PharMed® peristaltic pump tubing, size 14, Cole Parmer
Tissue culture flasks, Corning® 25 cm², Model 25110???
16 gauge hypodermic needles,
Glue Procedure Preparation of Liquid Level Control for Culture Flask 1. Cut the Leur-lock plastic fitting off of the 16 gauge needle. The inventors hold the needle in a small vice and cut the plastic fitting off with a hack saw. The needle is bent at the point it enters the flask to reduce the chance of the needle being accidentally pulled out of the chamber.

2. Mark the side of the flask at the intended liquid level with a marking pen.

3. Using a drill bit or a red hot gauge needle, make four holes in the sides of a Corning 25 (well above the intended liquid level) and one hole was placed in the top of the flask.

4. Three 16 gauge needles prepared as described in (1.) above were inserted into the three side holes in the flask such that the beveled needle opening faced the bottom of the flask. The needle should be inserted such that the needle opening will be constantly submerged at the intended liquid level. Glue the needles in place with glue.

5. Insert the cut end of a 16 gauge into the top hole of the flask such that the end of the needle is at the intended liquid level and the glue the needle in place with glue.

Planting Prototype Chamber with Cells

1. After the glue has dried, sterilize the flask by, for example, rinsing with Chlorox®, 95% ethanol, and sterile water.

2. Plant cells at the desired cell density.

3. Connect the needle together with two sterile pieces of PharMed® tubing to prevent entry of undesired organisms into the flask during the remaining steps.

4. Add 10 ml culture medium, for example Dulbecco's MEM, and the desired number and types of cells.

4. Place the flask in the $CO_2$-incubator to establish the desired $CO_2$-percentage. For example, 10% $CO_2$ may be used.

C. Connection of Prototype chamber to the Peristaltic Pump.

1. Connect the needle in the top of the flask to PharMed® size 14 tubing such that medium will be withdrawn from the flask through the needle.

2. Connect one needle in the side of the flask to PharMed® size 13 tubing such that medium will be withdrawn from the flask through the needle.

3. Connect the other two needles in the side of the flask with PharMed® size 13 tubing such that medium will be pumped into the flask through these needles.

Use of Chamber for Time Lapse Cinemicrography.

1. Focus the microscope on a region of the flask near an inlet needle to avoid the possible interference of the observations by cell debris. The fluid flowing through the inlet needle will push away debris for an area around the inlet.

2. Turn on the video camera and television monitor.

3. Focus the microscope and adjust lighting conditions.

4. Start the videotape recorder at the desired time lapse setting.

5. Program the timer to deliver a desired volume of medium at desired intervals.

Discussion of Use and Operation of Prototype Chamber

In making an exemplary model of their perfusable culture chamber, the inventors modified a standard 25 cm² culture flask so that medium could be perfused into the flask without altering the liquid level. Maintenance of a constant liquid level is essential in order to keep a cinemicrography chamber containing a specimen in focus. The prototype device operates as follows.

Medium is pumped into the chamber through two narrow bore (size 13) pieces of PharMed tubing. Medium is withdrawn from the chamber by one narrow bore size 13 tubing and one piece of larger bore size 14 tubing which is connected to the needle in the top of the flask. At the selected peristaltic pump speed (setting 4.0), each size 13 tubing has a flow rate of 2.6 ml/min while the size 14 tubing has a flow rate of 10.1 ml/min. Hence, the two size 13 inlet tubings have a net flow rate of 5.2 ml/min while the size 13 plus size 14 outlet tubing have a maximum flow rate of 12.7 ml/min. Liquid level is maintained at the level of the opening of the top needle for two reasons. First, medium can never be entirely depleted from the chamber since the two size 13 tubings are used to pump into the chamber and only one size tubing is used to pump from the bottom of the chamber, (once the liquid level falls below the level of the needle positioned in the top of the flask, no liquid can be withdrawn by the size 14 tubing. Second, medium can never go above the level of the top outflow needle since the maximum inflow rate is 5.2 ml/min while the maximum outflow rate is 12.7 ml/min. Note that the size 14 tubing port only with-draws medium from the chamber on an intermittent basis. Hence, this system maintains a constant liquid level.

There are several designs for a peristaltic pump heads currently on the market. Where two different sizes of tubing are used by one pump, it is advantageous that the pump use the independent pump heads rather than a single pump head that can accept several pieces of tubing. In the case of pump heads that accept several pieces of tubing, a screw or similar devise is used to apply pressure to tubing, and it is difficult to accurately set the flow rates of two different sized tubings.

The times at which the pump turns on and off and the interval during which it is active can easily be set by a household timer which supplies current to the pump during desired time intervals. The inventors have used an inexpensive timer allowing them to turn the pump on and off for intervals as short as 1 min. Using such a system, it is possible to automatically feed cultures with desired volume of medium at multiple times/day or continuously during the day.

The inventors have used the device described above to observe cells maintained at confluence for over a week without the specimen going out focus even when 200× magnification was used, thereby demonstrating the usefulness of the invention in time-lapse micrography studies.

The foregoing examples are provided to illustrate some of the preferred embodiments of the claimed invention. Of course, those of skill in the field will understand that many variations of the described invention are possible without departing from the spirit of the invention. All such variations are also considered to be within the scope of the invention.

References

The following articles and patents are incorporated by reference in pertinent part herein.

Carver, "Flask," U.S. Pat. No. 4,334,028, 1982.
Honda et al., "Tissue Culture Flask," U.S Pat. No. 5,139,952, 1992.
Lyman, "Tissue Culture Flask," U.S. Pat. No. 4,927,764, 1990.
Lyman, "Laboratory Flask," U.S. Pat No. 4,770,854, 1988.
Rose, "A Separable and Multipurpose Tissue Culture Chamber," *Tissue Culture Laboratory*, 1075–1083, 1954.
Sykes et al., "A New Chamber for Tissue Culture," *P.S.E.B.M.*, 125–127, 1958.

What is claimed is:

1. A perfusable culture device capable of maintaining a substantially constant culture media level and a substantially constant gas space above the culture media level when used in conjunction with a suitable pumping device comprising:

a chamber having an interior and exterior:

a culture media inlet system comprising at least one culture media inlet, the system being constructed, and positioned and arranged so as to have a total inlet flow capacity during use in conjunction with a suitable pumping device, the inlet leading from the exterior of the chamber to the interior of the chamber, the inlet further having a chamber interior port and a chamber exterior port, the chamber interior port of at least one culture media inlet being positioned below the desired culture media level;

a culture media outlet system comprising at least one culture media outlet, the system being constructed, and positioned and arrange so as to have a total outlet flow capacity during use in conjunction with a suitable pumping device, the outlet leading from the interior of the chamber to the exterior of the chamber, the outlet further having a chamber interior port and a chamber exterior port, the chamber interior port being positioned at a desired culture media level;

wherein, the system is constructed, and positioned and arranged so as to have a culture media total outlet flow capacity that is greater than the total culture media inlet flow capacity during use in conjunction with a suitable pumping device.

2. The perfusable culture device of claim 1, further defined as having at least two culture media inlets, each such inlet having a chamber interior port and a chamber exterior port, and the chamber interior port of at least one such inlet being positioned below the desired culture media level.

3. The perfusable culture device of claim 1, further defined as having at least two culture media outlets, each such outlet having a chamber interior port and a chamber exterior port.

4. The perfusable culture device of claim 1, wherein at least one culture media outlet enters the chamber in a gas space above the desired culture media level and has a chamber interior port positioned at the desired culture media level.

5. The perfusable culture device of claim 1, further comprising a culture media outlet which has a chamber interior port positioned below the desired culture media level during use.

6. The perfusable culture device of claim 5, wherein the culture media outlet having the chamber interior port positioned below the desired culture media level enters the chamber in the gas space above the desired culture media level.

7. The perfusable culture device of claim 1, wherein the culture media inlet enters the chamber in a gas space above the desired culture media level.

8. The perfusable culture device of claim 1, wherein the chamber is further defined as a culture flask.

9. The perfusable culture device of claim 1, wherein the chamber has optical qualities allowing for microscopic viewing of contents of the chamber during use.

10. The perfusable culture device of claim 1, further comprising a pump attached to the chamber exterior port of each culture media outlet, the pump pumping at the culture media outlet capacity during use.

11. The perfusable culture device of claim 10, further comprising a pump attached to the chamber exterior port of each culture media inlet, the pump pumping at the culture media inlet capacity during use.

12. The perfusable culture device of claim 10, wherein the pump is a peristaltic pump.

13. The perfusable culture device of claim 12, wherein the peristaltic pump is a multihead peristaltic pump.

14. The perfusable culture device of claim 10, wherein each culture media inlet chamber exterior port and each culture media outlet chamber exterior port is attached its own pump head.

15. A method of culturing cells at a high density comprising:

obtaining a perfusable culture device capable of maintaining a substantially constant culture media level when used in conjunction with a suitable pumping device comprising:

a chamber having an interior and exterior;

a culture media inlet system comprising at least one culture media inlet, the system being constructed, and positioned and arranged so as to have a total inlet flow capacity during use in conjunction with a suitable pumping device, the inlet leading from the exterior of the chamber to the interior of the chamber, the inlet further having a chamber interior port and a chamber exterior port;

a culture media outlet system comprising at least one culture media outlet, the system being constructed, and positioned and arranged so as to have a total outlet flow capacity during use in conjunction with a suitable pumping device, the outlet leading from the interior of the chamber to the exterior of the chamber, the outlet further having a chamber interior port and a chamber exterior port, the chamber interior port being positioned at a desired culture media level;

wherein, the system is constructed, and positioned and arranged so as to have a culture media total outlet flow capacity that is greater than the total culture media inlet flow capacity during use in conjunction with a suitable pumping device;

placing culture media and cell to be cultured in the perfusable culture device;

attaching the culture media outlet(s) and culture media inlet(s) to a pump;

perfusing the chamber by pumping culture media into the chamber through the culture media inlet(s) and pumping culture media out of the chamber through the culture media outlet(s) thereby maintaining the desired media level in the chamber; and allowing cells to grow to a desired density in the perfusable culture device.

16. A method for performing time-lapse micrography of cell cultures comprising:

employing the method of claim 15; and recording the course of the cell culturing with a camera.

17. The method of claim 16, wherein the camera is a videotape camera.

18. The method of claim 15, wherein the perfusable culture device comprises at least one culture media outlet that enters the chamber in a gas space above the desired culture media level and has a chamber interior port positioned at the desired culture media level.

19. The method of claim 15, wherein the chamber interior port of at least one culture media inlet is positioned below the desired culture media level.

* * * * *

UNITED STATES PATENT AND TRADEMARK OFFICE
CERTIFICATE OF CORRECTION

PATENT NO. : 5,565,353

DATED : October 15, 1996

INVENTOR(S) : Klebe et al.

It is certified that error appears in the above-identified patent and that said Letters Patent is hereby corrected as shown below:

In claim 1, column 11, line 65, delete "arrange" and insert
--arranged-- therefor.

Signed and Sealed this

Seventeenth Day of December, 1996

Attest:

BRUCE LEHMAN

*Attesting Officer*  *Commissioner of Patents and Trademarks*